(12) United States Patent
Abe

(10) Patent No.: US 12,194,117 B2
(45) Date of Patent: Jan. 14, 2025

(54) RESIN BEADS, METHOD FOR PRODUCING RESIN BEADS, AND PRODUCT USING RESIN BEADS

(71) Applicant: DAINICHISEIKA COLOR & CHEMICALS MFG. CO., LTD., Tokyo (JP)

(72) Inventor: Takashi Abe, Tokyo (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

(21) Appl. No.: 18/257,531

(22) PCT Filed: Sep. 22, 2021

(86) PCT No.: PCT/JP2021/034810
§ 371 (c)(1),
(2) Date: Jun. 14, 2023

(87) PCT Pub. No.: WO2022/137679
PCT Pub. Date: Jun. 30, 2022

(65) Prior Publication Data
US 2024/0041710 A1 Feb. 8, 2024

(30) Foreign Application Priority Data
Dec. 23, 2020 (JP) .................. 2020-213456

(51) Int. Cl.
*A61K 8/02* (2006.01)
*A61K 8/73* (2006.01)
(Continued)

(52) U.S. Cl.
CPC .............. *A61K 8/025* (2013.01); *A61K 8/731* (2013.01); *A61Q 1/02* (2013.01); *A61Q 19/007* (2013.01);
(Continued)

(58) Field of Classification Search
None
See application file for complete search history.

(56) References Cited

U.S. PATENT DOCUMENTS

| 4,663,447 A | 5/1987 | Yamazaki et al. |
| 4,968,350 A | 11/1990 | Bindschaedler et al. |

(Continued)

FOREIGN PATENT DOCUMENTS

| CN | 102911379 | 2/2013 |
| EP | 0309527 | 4/1989 |

(Continued)

OTHER PUBLICATIONS

English translation of JP-2010155982-A (Year: 2010).*
(Continued)

*Primary Examiner* — Nicole P Babson
(74) *Attorney, Agent, or Firm* — HSML P.C.

(57) ABSTRACT

The present invention provides resin beads that can provide various types of products, such as a cosmetic having excellent tactile impression, such as spreadability on the skin, moist feeling, and softness, and having high stability such that such tactile impression is kept over a long period of time, that can be substituted for resin particles composed of a synthetic material derived from petroleum, and that have favorable biodegradability. The present invention also provides various types of products, such as a cosmetic, using the resin beads. The resin beads are obtained by surface-treating, with a solid surface treatment agent, core beads formed with a resin containing cellulose as a main component, and have a cumulative 50% particle size on a volume basis of 50 μm or smaller, a degree of sphericity of 0.7 to 1.0, a degree of surface smoothness of 70 to 100%, and a degree of crystallinity of 60% or less. In addition, the present invention provides a product of any one of a cosmetic, a dermatological preparation, a paint, a shaped article, a film, a (Continued)

coating agent, and a resin composition which contain the resin beads.

17 Claims, 1 Drawing Sheet

(51) Int. Cl.
  *A61Q 1/02* (2006.01)
  *A61Q 19/00* (2006.01)
  *C08J 3/16* (2006.01)
  *C08J 7/14* (2006.01)
  *C08L 1/12* (2006.01)
  *C08L 1/14* (2006.01)
(52) U.S. Cl.
  CPC .................. *C08J 3/16* (2013.01); *C08J 7/14* (2013.01); *C08L 1/12* (2013.01); *C08L 1/14* (2013.01); *A61K 2800/614* (2013.01); *A61K 2800/654* (2013.01); *C08J 2301/12* (2013.01)

(56) References Cited

U.S. PATENT DOCUMENTS

| | | | |
|---|---|---|---|
| 5,244,734 | A | 9/1993 | Okuma et al. |
| 5,245,024 | A | 9/1993 | Scarpa et al. |
| 5,972,507 | A | 10/1999 | Morimoto et al. |
| 6,225,461 | B1 | 5/2001 | Akimoto et al. |
| 6,541,627 | B1 | 4/2003 | Ono et al. |
| 6,571,802 | B1 | 6/2003 | Yamashita |
| 8,192,748 | B2 | 6/2012 | Kuroda |
| 11,548,999 | B2 | 1/2023 | Abe |
| 11,628,134 | B2 | 4/2023 | Kobayashi et al. |
| 2003/0012941 | A1 | 1/2003 | Fujita et al. |
| 2005/0118121 | A1 | 6/2005 | Kuroda |
| 2005/0203278 | A1 | 9/2005 | McCreight et al. |
| 2008/0131597 | A1 | 6/2008 | Takehara et al. |
| 2009/0044942 | A1 | 2/2009 | Gupta |
| 2009/0280186 | A1 | 11/2009 | Yaginuma et al. |
| 2010/0087552 | A1 | 4/2010 | Shiomi et al. |
| 2010/0178332 | A1 | 7/2010 | Kakizawa et al. |
| 2011/0282049 | A1 | 11/2011 | Shelton et al. |
| 2012/0027825 | A1 | 2/2012 | Benoit et al. |
| 2016/0303032 | A1 | 10/2016 | Kamei |
| 2020/0179261 | A1 | 6/2020 | Kobayashi et al. |
| 2020/0299488 | A1 | 9/2020 | Kobayashi et al. |
| 2022/0025131 | A1 | 1/2022 | Shibata et al. |
| 2022/0142900 | A1* | 5/2022 | Kobayashi ............... C08J 3/128 |
| 2022/0154356 | A1 | 5/2022 | Manabe |
| 2022/0267573 | A1 | 8/2022 | Abe |
| 2022/0275163 | A1 | 9/2022 | Shibata et al. |
| 2023/0136180 | A1 | 5/2023 | Abe |
| 2023/0303782 | A1 | 9/2023 | Abe |
| 2024/0247112 | A1 | 7/2024 | Abe |

FOREIGN PATENT DOCUMENTS

| | | |
|---|---|---|
| EP | 0750007 | 12/1996 |
| EP | 3613794 | 2/2020 |
| EP | 3943530 | 1/2022 |
| EP | 3998300 | 5/2022 |
| EP | 4116357 | 1/2023 |
| EP | 4209514 | 7/2023 |
| EP | 4234043 | 8/2023 |
| JP | 49-019183 | 2/1974 |
| JP | 50-041954 | 4/1975 |
| JP | 51-090352 | 8/1976 |
| JP | 55-028763 | 2/1980 |
| JP | 59-219333 | 12/1984 |
| JP | 60-155245 | 8/1985 |
| JP | 62-253601 | 11/1987 |
| JP | 63-068645 | 3/1988 |
| JP | 63-095237 | 4/1988 |
| JP | 06-254373 | 9/1994 |
| JP | 11-181147 | 7/1999 |
| JP | 2931810 | 8/1999 |
| JP | 11-279201 | 10/1999 |
| JP | 2000-309503 | 11/2000 |
| JP | 2000-309508 | 11/2000 |
| JP | 2002-205917 | 7/2002 |
| JP | 2002-363445 | 12/2002 |
| JP | 2003-146829 | 5/2003 |
| JP | 2003-252903 | 9/2003 |
| JP | 2005-264120 | 9/2005 |
| JP | 2006-131875 | 5/2006 |
| JP | 2006-523752 | 10/2006 |
| JP | 2006-328245 | 12/2006 |
| JP | 2007-528436 | 10/2007 |
| JP | 2007-291035 | 11/2007 |
| JP | 4076955 | 4/2008 |
| JP | 2010-077111 | 4/2010 |
| JP | 2010155982 A * | 7/2010 |
| JP | 2012-092191 | 5/2012 |
| JP | 2013-221000 | 10/2013 |
| JP | 2014-028785 | 2/2014 |
| JP | 2014-224183 | 12/2014 |
| JP | 2015-117190 | 6/2015 |
| JP | 2017-052961 | 3/2017 |
| JP | 2018-008392 | 1/2018 |
| JP | 2018-052909 | 4/2018 |
| JP | 2018-127579 | 8/2018 |
| JP | 2019-031631 | 2/2019 |
| JP | 6609726 | 11/2019 |
| JP | 2020-075878 | 5/2020 |
| JP | 6694559 | 5/2020 |
| JP | 2020-109074 | 7/2020 |
| JP | 2020-132616 | 8/2020 |
| JP | 2020-152851 | 9/2020 |
| JP | 6872068 | 5/2021 |
| WO | 88/08011 | 10/1988 |
| WO | 1999/028350 | 6/1999 |
| WO | 2003/075863 | 9/2003 |
| WO | 2004/083253 | 9/2004 |
| WO | 2009/123148 | 10/2009 |
| WO | 2010/067037 | 6/2010 |
| WO | 2011/105535 | 9/2011 |
| WO | 2012/133018 | 10/2012 |
| WO | 2015/029790 | 3/2015 |
| WO | 2016/013568 | 1/2016 |
| WO | 2019/156116 | 8/2019 |
| WO | 2020/137017 | 7/2020 |
| WO | 2020/188698 | 9/2020 |

OTHER PUBLICATIONS

English translation of JP-2003146829-A (Year: 2003).*
Sakai Chemical "Metallic Soap" <https://www.sakai-chem.co.jp/en/products_services_plastic_additive.php> (Year: 2016).*
International Search Report, issued in the corresponding PCT application No. PCT/JP2021/034810, dated Nov. 30, 2021, 5 pages (including translation).
International Search Report, issued in the related PCT application No. PCT/JP2020/026551, dated Sep. 24, 2020, 7 pages (including translation).
Extended European Search Report, issued in the related European Patent Application No. 20837372.0, dated Jul. 29, 2022, 10 pages.
"Novel colored complex cellulose beads", Society of Cosmetic Scientists, 2003, 1 page.
Brazilian Office Action, issued in the related Brazilian Patent Application No. 112022000453-2, dated Jun. 10, 2022, 8 pages.
International Search Report, issued in the related PCT application No. PCT/JP2021/007183, dated May 18, 2021, 5 pages (including machine translation).
"Measuring method for specific gravity of solid", JIS Handbook 31 Chemical analysis, pp. 751-755, Japanese Standards Association, Apr. 20, 1997, cited in the Notice of Reasons for Revocation (A concise explanation of relevance provided in Notice of Reasons for Revocation for JP patent application 2020-036983, dated Aug. 20, 2021).
Technical Data Sheet, "Cellulose Acetate Propionate CAP-482-0. 5", Eastman, cited in the Notice of Reasons for Revocation (dated Mar. 30, 2022), 4 pages, 2021.

(56) References Cited

OTHER PUBLICATIONS

Notice of Reasons for Revocation of JP patent 6779400 (JP patent application 2020-036983), issued in the Trial/Appeal Opposition No. JP 2021-700373, dated Aug. 20, 2021, 41 pages (including machine translation).
Notice of Reasons for Revocation of JP patent 6779400 (JP patent application 2020-036983) with allowance of amendments, issued in the Trial/Appeal Opposition No. JP 2021-700373, dated Mar. 30, 2022, 57 pages (including machine translation).
El-Habashy et al., "Ethyl cellulose nanoparticles as a platform to decrease ulcerogenic potential of piroxicam: formulation and in vitro/in vivo evaluation", International Journal of Nanomedicine, Original Research, 2016, pp. 2369-2380.
Scarfato et al., "Quercetin microspheres by solvent evaporation: Preparation, characterization and release behavior", Journal of Applied Science, vol. 109, 2008, pp. 2994-3001.
Extended European Search Report, issued in the corresponding European Patent Application No. 21864062.1, dated Oct. 13, 2023, 9 pages.
Extended European Search Report, issued in the corresponding European Patent Application No. 21764155.4, dated Oct. 13, 2023, 8 pages.
International Search Report, issued in the corresponding PCT application No. PCT/JP2021/029501, dated Sep. 21, 2021, 7 pages (including machine translation).
Extended European Search Report, issued in the related European patent application No. 21909837.3, dated Mar. 27, 2024, 8 pages.
U.S. Appl. No. 17/597,111, filed Dec. 27, 2021, U.S. Publication No. 2022/0267573, (issued as U.S. Pat. No. 11,548,999 on Jan. 10, 2023.
U.S. Appl. No. 17/905,233, filed Aug. 29, 2022, U.S. Publication No. 2023/0136180, (issued as U.S. Pat. No. 11,998,630 on Jun. 4, 2024.
U.S. Appl. No. 18/042,739, filed Feb. 23, 2023, U.S. Publication No. 2023/0303782, (issued as U.S. Pat. No. 11,926,718 on Jun. 4, 2024.
U.S. Appl. No. 18/435,401, filed Feb. 7, 2024, U.S. Publication No. 2024/0247112.
U.S. Appl. No. 18/834,929, filed Jul. 31, 2024.
International Search Report, issued in the related PCT application No. PCT/JP2022/044145, dated Feb. 21, 2023, 5 pages (including translation).
Shiho Suzuki, U.S. Appl. No. 18/834,929, filed Jul. 31, 2024 and entitled "Water Repellent Cellulose Beads, Manufacturing Method Therefor, and Cosmetic", 24 pages.

\* cited by examiner

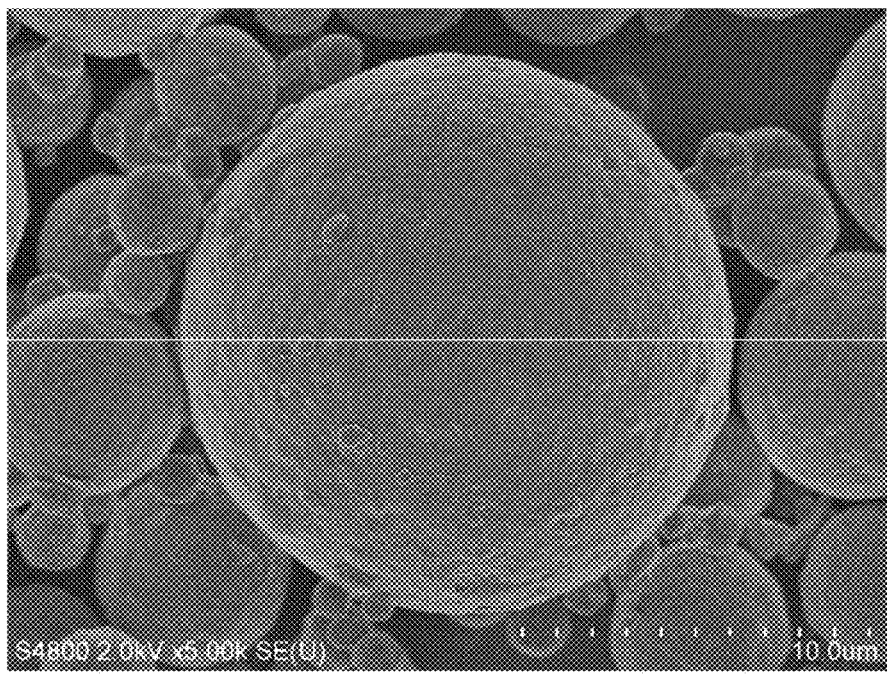

RESIN BEADS, METHOD FOR PRODUCING RESIN BEADS, AND PRODUCT USING RESIN BEADS

TECHNICAL FIELD

The present invention relates to resin beads formed with a resin containing cellulose as a main component, a method for producing the resin beads, and products, such as a cosmetic, obtained using the resin beads.

BACKGROUND ART

In the past, resin beads have been used in various fields, such as a matting agent, a slipping agent, and an antiblocking agent, from the properties derived from the spherical shape. Further, various resin powders (resin particles), such as resin beads, have been used in order to improve the properties, such as spreadability of cosmetics for makeup. However, materials for forming resin beads to be blended in cosmetics have been changed from synthetic materials derived from petroleum to natural materials due to the problems and the like, such as marine pollution caused by microplastics, in recent years.

For example, powdery cellulose useful as a scrubbing agent has been proposed as spherical resin particles composed of a natural material (Patent Literature 1). Further, cellulose derivative fine particles (Patent Literature 2) which are used for a diagnostic drug and a spherical cellulose powder (Patent Literature 3) which is used for cosmetics have been proposed. Furthermore, a cellulose composite powder in which feeling on the skin has been improved, and the like have been proposed (Patent Literatures 4 and 5).

CITATION LIST

Patent Literature

Patent Literature 1: Japanese Patent Laid-Open No. 2018-052909
Patent Literature 2: International Publication No. WO 2009/123148
Patent Literature 3: Japanese Patent Laid-Open No. 2013-221000
Patent Literature 4: Japanese Patent Laid-Open No. 2003-146829
Patent Literature 5: Japanese Patent Laid-Open No. 2020-075878

SUMMARY OF INVENTION

Technical Problem

However, the powdery cellulose and the like proposed in Patent Literatures 1 and 2 do not have a suitable particle size as a material to be blended in cosmetics for makeup or skin care. In addition, copper ammonia needs to be used when the cellulose derivative fine particles proposed in Patent Literature 2 are produced, and therefore the cellulose derivative fine particles cannot necessarily be said to be suitable as a material for cosmetics in which heavy metals are desired to be reduced as much as possible. Further, the cellulose powder and the like proposed in Patent Literatures 3 have a large ratio of the major axis to the minor axis with regard to the particle size, and the spreadability on the skin and the tactile impression cannot be said to be favorable when the cellulose powder and the like are blended in cosmetics, so that rough surfaces have been likely to be felt. Furthermore, in the cellulose composite powder and the like proposed in Patent Literatures 4 and 5, the degree of circularity of a base material to be treated is low, and therefore when such a base material to be treated is surface-treated, it has been difficult to obtain a cosmetic or the like having excellent spreadability on the skin and excellent tactile impression.

With regard to the cellulose powder and the like proposed so far, the spreadability on the skin cannot be said to be favorable so much, and the tactile impression is smooth and dry instead of soft and moist tactile impression felt in silicone beads, nylon beads, and the like, as required in the market. Further, in cosmetics prepared using the conventional cellulose powder and the like, the tactile impression cannot be kept over a long period of time, and therefore there has been room for improvements in stability as a product.

The present invention has been completed in view of the problems of such conventional techniques, and an object of the present invention is to provide: resin beads that can provide various types of products, such as a cosmetic having excellent tactile impression, such as spreadability on the skin, moist feeling, and softness, and having high stability such that such tactile impression is kept over a long period of time, that can be substituted for resin particles composed of a synthetic material derived from petroleum, and that have favorable biodegradability; and various types of products, such as a cosmetic, using the resin beads. Further, another object of the present invention is to provide a method for producing resin beads that can provide various types of products, such as a cosmetic having excellent tactile impression, such as spreadability on the skin, moist feeling, and softness, and having high stability such that such tactile impression is kept over a long period of time, that can be substituted for resin particles composed of a synthetic material derived from petroleum, and that have favorable biodegradability.

Solution to Problem

That is, according to the present invention, resin beads, described below, are provided.

[1] Resin beads obtained by surface-treating, with a solid surface treatment agent, core beads formed with a resin comprising cellulose as a main component, wherein the resin beads have a cumulative 50% particle size on a volume basis of 50 μm or smaller, a degree of sphericity of 0.7 to 1.0, a degree of surface smoothness of 70 to 100%, and a degree of crystallinity of 60% or less.
[2] The resin beads according to [1], wherein the surface treatment agent is a plate-shaped substance.
[3] The resin beads according to [2], wherein the plate-shaped substance has an aspect ratio (major diameter/minor diameter) of 2 or more and 10 or less.
[4] The resin beads according to any one of [1] to [3], wherein the surface treatment agent is at least one lipophilic treatment agent selected from the group consisting of metallic soap-based treatment agents, amino acid-based treatment agents, phospholipid-based treatment agents, glycolipid-based treatment agents, complex lipid-based treatment agents, and ceramide-based treatment agents.
[5] The resin beads according to [4], wherein the metallic soap-based treatment agents are metal salts of stearic acid.

[6] The resin beads according to any one of [1] to [5], having a biodegradation rate for 5 days, as measured in accordance with JIS K6950:2000 (ISO 14851:1999), of 10% or more.

[7] The resin beads according to any one of [1] to [6], having a cumulative 90% particle size on a volume basis of 40 μm or smaller.

[8] The resin beads according to any one of [1] to [7], having a cumulative 10% particle size on a volume basis of 0.1 μm or larger.

[9] The resin beads according to any one of [1] to [8], wherein a CV value of the particle size is 10 to 90%.

[10] The resin beads according to any one of [1] to [9], wherein a content of the cellulose in the resin forming the core beads is 50 to 100% by mass.

In addition, according to the present invention, a method for producing resin beads, described below, is provided.

[11] A method for producing resin beads having a cumulative 50% particle size on a volume basis of 50 μm or smaller, a degree of sphericity of 0.7 to 1.0, a degree of surface smoothness of 70 to 100%, and a degree of crystallinity of 60% or less, the method comprising: a step of mixing an oil phase comprising a cellulose ester and an organic solvent that dissolves the cellulose ester and has a solubility to 100 g of water at 25° C. of 0.1 to 50.0 g with an aqueous phase comprising a dispersion stabilizer, thereby preparing a suspension comprising oil droplets comprising the cellulose ester and the organic solvent; a step of adding water to the suspension, thereby contracting the oil droplets and forming resin particles; a step of treating the resin particles under an acidic condition, or an alkaline condition of a pH of 13 or lower, thereby hydrolyzing at least part of ester bonds in the cellulose ester to obtain core beads formed with a resin comprising cellulose as a main component; and a step of surface-treating the core beads with a surface treatment agent.

[12] The method for producing resin beads according to [11], wherein the cellulose ester is at least one selected from the group consisting of cellulose acetate, cellulose propionate, cellulose acetate propionate, cellulose butyrate, and cellulose acetate butyrate.

[13] The method for producing resin beads according to [11] or [12], wherein the dispersion stabilizer is a water-soluble polymer.

[14] The method for producing resin beads according to any one of [11] to [13], wherein 100 parts by mass of the core beads are surface-treated with 0.1 to 30 parts by mass of the surface treatment agent.

[15] The method for producing resin beads according to any one of [11] to [14], wherein the surface treatment agent is a plate-shaped substance.

[16] The method for producing the resin beads according to [15], wherein the plate-shaped substance has an aspect ratio (major axis/minor axis) of 10 or less.

[17] The method for producing resin beads according to any one of [11] to [16], wherein the core beads are surface-treated with the surface treatment agent by a dry blending method or a mechanochemical method.

Further, according to the present invention, a product, described below, is provided.

[18] A product of any one of a cosmetic, a dermatological preparation, a paint, a shaped article, a film, a coating agent, and a resin composition each comprising resin beads, wherein the resin beads are the resin beads according to any one of [1] to [10].

Advantageous Effects of Invention

The present invention can provide: resin beads that can provide various types of products, such as a cosmetic having excellent tactile impression, such as spreadability on the skin, moist feeling, and softness, and having high stability such that such tactile impression is kept over a long period of time, that can be substituted for resin particles composed of a synthetic material derived from petroleum, and that have favorable biodegradability; and various types of products, such as a cosmetic, using the resin beads. Further, the present invention can provide a method for producing resin beads that can provide various types of products, such as a cosmetic having excellent tactile impression, such as spreadability on the skin, moist feeling, and softness, and having high stability such that such tactile impression is kept over a long period of time, that can be substituted for resin particles composed of a synthetic material derived from petroleum, and that have favorable biodegradability.

BRIEF DESCRIPTION OF DRAWINGS

The FIGURE is an electron micrograph showing a state of surfaces of resin beads produced in Example 1.

DESCRIPTION OF EMBODIMENTS

Hereinafter, embodiments of the present invention will be described, but the present invention is not limited to the following embodiments. Note that various physical property values as used herein are values at normal temperature (25° C.) unless otherwise noted.

The present inventors have conducted various studies on resin beads that can provide various types of products, such as a cosmetic having excellent tactile impression, such as spreadability on the skin, moist feeling, and softness, and having high stability such that such tactile impression is kept over a long period of time, and that are composed of a natural material, and on the method for producing the resin beads. As a result, the present inventors have found that by adopting the constitution described below, resin beads that are substantially formed with a natural material and that can provide various types of products, such as a cosmetic imparted with the above-described various properties, can be obtained. That is, the resin beads of the present invention are obtained by surface-treating, with a surface treatment agent, core beads formed with a resin containing cellulose as a main component, and have a cumulative 50% particle size on a volume basis of 50 μm or smaller, a degree of sphericity of 0.7 to 1.0, a degree of surface smoothness of 70 to 100%, and a degree of crystallinity of 60% or less.

The cumulative 50% particle size (median size; $D_{50}$) on a volume basis of the resin beads is 50 μm or smaller, preferably 30 μm or smaller, more preferably 0.5 to 28 μm, and particularly preferably 1 to 25 μm. By setting $D_{50}$ to the above-described range, the slipperiness and soft-focus performance, which are required in resin beads to be blended in a cosmetic and the like, can effectively be exhibited.

The cumulative 90% particle size ($D_{90}$) on a volume basis of the resin beads is preferably 40 μm or smaller, more preferably 30 μm or smaller, and particularly preferably 5 to 25 μm. Further, the cumulative 10% particle size ($D_{10}$) on a volume basis of the resin beads is preferably 0.1 μm or larger, more preferably 0.5 μm or larger, and still more preferably 1.5 to 10 μm. Then, the CV value (coefficient of variation) of the particle size of the resin beads is preferably 10 to 90%, more preferably 15 to 75%, and particularly preferably 20 to 60%. By setting $D_{90}$, $D_{10}$, and the CV value to the above-described ranges respectively, smoothness without feeling of a foreign body, which is required in resin beads to be blended in a cosmetic and the like, can be exhibited, and a cosmetic such that getting into wrinkles are suppressed can be made.

The degree of sphericity of the resin beads is 0.7 to 1.0, preferably 0.75 to 1.0, more preferably 0.8 to 1.0, and particularly preferably 0.85 to 1.0. By setting the degree of sphericity to the above-described range, spreadability on the skin and excellent tactile impression, which are required in resin beads to be blended in a cosmetic and the like, can effectively be exhibited.

The degree of sphericity, which is an index of whether the resin beads have a perfectly spherical shape or not, can be measured and calculated according to the procedure described below. Firstly, a SEM image of the resin beads, taken with a scanning electron microscope (SEM), is subjected to image analysis to calculate the degree of circularity C for each resin bead from the following formula (1). Then, the arithmetic average value of the degrees of circularity C for 10 or more resin beads arbitrarily selected is defined as the degree of sphericity.

$$C=(4\pi S_1)/(L^2) \quad (1)$$

In the formula (1), $S_1$ represents the area (projected area) of each resin bead in the image, and L represents the length of the outer peripheral part of the resin bead in the image. As the value of the degree of circularity C is closer to 1, the shape of a particle is closer to a perfect sphere.

The degree of surface smoothness of the resin beads is 70 to 100%, preferably 80% to 100%, and more preferably 90 to 100%. By setting the degree of surface smoothness to the above-described range, favorable tactile impression and spreadability on the skin, which are required in resin beads to be blended in a cosmetic and the like, can effectively be exhibited.

The degree of surface smoothness of the resin beads can be measured according to the procedure described below. That is, a SEM image (×5,000) of the resin beads, taken with a scanning electron microscope (SEM), is observed to calculate the degree of smoothness M for each resin bead from the following formula (2). Then, the arithmetic average value of the degrees of smoothness M for 10 or more resin beads arbitrarily selected is defined as the degree of surface smoothness. As the value of the degree of smoothness M is closer to 100, the surface of a particle is closer to be smooth.

$$M=(1-(S_3)/(S_2))\times 100 \quad (2)$$

In the formula (2), $S_2$ represents the area (projected area) of each resin bead in the image, and in the case where a resin bead and a circle that approximates the resin bead are overlapped, $S_3$ represents, in the regions formed by the contour of the resin bead and the contour of the circle, the sum total of the areas of regions that exist inside the contour of the overlapped circle and the areas of regions that exist outside the contour of the overlapped circle.

The degree of crystallinity of the resin beads is 60% or less, preferably 50% or less, and still more preferably 40% or less. By setting the degree of crystallinity within the above-described range, stability that is required in resin beads to be blended in a cosmetic and the like can be enhanced, and tactile impression and lipophilicity can be improved. When the degree of crystallinity of the resin beads is more than 60%, the stability of a product, such as a cosmetic, may be somewhat lowered. It is considered that this is because in the case where cellulose having high crystallinity is surface-treated, the effect of hydrogen bond between the surface treatment agent and the cellulose is somewhat weaker than that in the case where cellulose having low crystallinity is surface treated. The lower limit of the degree of crystallinity is not particularly limited but may be 0.1% or more.

The degree of crystallinity of the resin beads can be measured and calculated according to the procedure described below. That is, peak intensity (P) at around $2\theta=12°$ and peak intensity (PB) of the base line there are determined among the cellulose type II diffraction peaks of the resin beads, measured with an X-ray diffractometer. Then, the degree of crystallinity C of the resin beads is calculated from the following formula (3). As the value of the degree of crystallinity C is closer to 100, the crystallinity of the resin beads is higher. Note that according to this measurement-calculation method, the degree of crystallinity of the resin beads (subjected to the surface treatment) and the degree of crystallinity of the core beads (before the surface treatment) substantially take the same value.

$$C\{(P-PB)/PB\}\times 100 \quad (3)$$

The degree of solidity of the resin beads is preferably 50 to 100% by volume, more preferably 60 to 100% by volume, and particularly preferably 70 to 100% by volume. By setting the degree of solidity within the above-described range, the stability that is required in resin beads to be blended in a cosmetic and the like can be enhanced more, and the transparency can be improved. When the degree of solidity of the resin beads is less than 50% by volume, light scattering occurs due to empty regions, so that the transparency is likely to lower. In addition, when the degree of solidity lowers, the oil absorption and strength are changed, or the resin beads are likely to become nonuniform because a liquid or particles penetrate into the empty regions. For this reason, when resin beads having a low degree of solidity are blended in a product, such as a cosmetic, the product stability may be somewhat lowered.

The degree of solidity of the resin beads can be measured and calculated according to the procedure described below. Firstly, a SEM image of sections of the resin beads, taken with a scanning electron microscope (SEM), is subjected to image analysis to calculate the volume of the part filled with the resin for each resin bead. Then, the average value of the volumes of the parts filled with the resin for 10 or more resin beads arbitrarily selected is defined as the degree of solidity (% by volume).

The biodegradation rate for 5 days of the resin beads is preferably 10% or more, more preferably 20% or more, and particularly preferably 30% or more. The resin beads of the present invention have a high biodegradation rate, as described above, and therefore have excellent biodegradability. For this reason, the resin beads of the present invention are useful as resin beads to be blended in a cosmetic and the like in which exhibiting favorable biodegradability is required. Note that by producing the resin beads according to the production method which will be described later, the resin beads having more excellent biodegradability can be obtained than in the case where the resin beads are produced according to another conventional production method in spite of the fact that the resin beads are formed using the same resin containing cellulose as a main component. The reason has not necessarily been made clear yet.

The biodegradation rate for 5 days of the resin beads is measured in accordance with JIS K6950:2000 (ISO 14851:1999). More specifically, the biodegradation rate for 5 days of the resin beads is measured and calculated by conducting a test under conditions (measurement of BOD using a closed system oxygen consumption measuring apparatus) shown below.

Inoculum: aerobic reactor sludge in sewage treatment plant that mainly treats domestic wastewater
Reference material: microcrystalline cellulose
Concentration of test material: 100 mg/L
Concentration of reference material: 100 mg/L
Concentration of inoculum: 150 mg/L
Amount of test solution: 300 mL
Test temperature: 25±1° C.
Cultivation period: 30 days The biodegradation rates of the test material and the reference material can be calculated from the following formula.

$$\text{Biodegradation rate (\%)} = (BODO - BODB)/ThOD \times 100$$

BODO (mg): biochemical oxygen demand of test material
BODB (mg): average biochemical oxygen demand of reference material
ThOD (mg): Theoretical maximum oxygen demand necessary for oxidizing test material The core beads are formed with a resin containing cellulose as a main component. The resin for forming the core beads may contain a cellulose derivative, such as a cellulose ester, in addition to the cellulose. The content of the cellulose in the resin for forming the core beads is preferably 50 to 100% by mass because the biodegradability of the resin beads is further improved, and is more preferably 60 to 100% by mass, particularly preferably 70 to 100% by mass, and most preferably 90 to 100% by mass. The cellulose may be blended in the resin for forming the core beads in advance, or may be formed by chemically modifying (for example, hydrolyzing) a cellulose derivative, such as a cellulose ester.

The core beads may contain at least any one of a pigment and a dye according to the application. To obtain the core beads containing a pigment or a dye, the suspension may be prepared using, for example, the oil phase further containing at least any one of the pigment and the dye. Examples of the pigment include metal oxides, such as titanium dioxide, zinc oxide, Bengala, yellow iron oxide, and black iron oxide, and besides, Food Yellow No. 4, Food Red No. 202, and Food Blue No. 1, which are Japanese names of certified colors, and carbon black. In addition, extender pigments, such as mica, talc, kaolin, and calcium carbonate, can also be used. Examples of the dye include Food Red No. 104, Food Yellow No. 5, and Food Blue No. 1.

The core beads preferably contain: a pigment; and at least any one of a surfactant, a dispersant, and a polymer dispersant. In addition, the pigment is preferably a treated pigment treated with at least one selected from the group consisting of a silicone, a fatty acid, a metal salt of a fatty acid, an amino acid, a metal salt of an amino acid, fat and oil, and a lipid.

The core beads may contain at least any one of an ultraviolet absorbing agent and an ultraviolet scattering agent according to the application. To obtain the core beads containing an ultraviolet absorbing agent or an ultraviolet scattering agent, the suspension may be prepared using, for example, the oil phase further containing at least any one of the ultraviolet absorbing agent and the ultraviolet scattering agent. Examples of the ultraviolet absorbing agent and the like include fine particle titanium dioxide, fine particle zinc oxide, a cinnamic acid-based ultraviolet absorbing agent, and a dibenzoylmethane-based ultraviolet absorbing agent.

The resin beads of the present invention are obtained by surface-treating, with a surface treatment agent, core beads formed with a resin containing cellulose as a main component. It is inferred that when the core beads are surface-treated with a surface treatment agent, some kind of coating layer is formed on at least a part of the surfaces of the core beads due to adhesion, support, bonding, or the like of the surface treatment agent. However, it is substantially difficult or impossible to analyze and check the state of adhesion of the surface treatment agent or the state (range, adhesion amount, thickness, or the like) of the coating layer formed due to the adhesion or the like of the surface treatment agent to the core beads.

A conventionally known treatment agent can be used as the surface treatment agent. Examples of the surface treatment agent include a metal hydroxide, a silicone resin, a siloxane-based resin, a hydrophobic silica, a fatty acid, a metal salt of a fatty acid, an amino acid-based substance, complex lipids such as a phospholipid and a glycolipid, a surfactant, a wax, a higher alcohol, talc, calcium carbonate, alumina, titanium dioxide, and zinc oxide. When the surfaces of the core beads are treated with any of these surface treatment agents, a treatment, such as heating, baking, crosslinking, and polymerization, may be performed as necessary.

A lipophilic treatment agent is preferably used as the surface treatment agent. By surface-treating the core beads with a lipophilic treatment agent, resin beads that can provide a product, such as a cosmetic having high lipophilicity (water repellency) and having more excellent stability, can be made. Examples of the lipophilic treatment agent include a metallic soap-based treatment agent, an amino acid-based treatment agent, a phospholipid-based treatment agent, a glycolipid-based treatment agent, complex lipid-based treatment agent, and a ceramide-based treatment agent. Among others, a metallic soap-based treatment agent and an amino acid-based treatment agent are preferable. Examples of the metallic soap-based treatment agent include a metal salt of stearic acid, a metal salt of palmitic acid, a metal salt of myristic acid, a metal salt of lauric acid, a metal salt of capric acid, a metal salt of caprylic acid, a metal salt of behenic acid, a metal salt of oleic acid, and a metal salt of 12-hydroxystearic acid. Among others, a metal salt of stearic acid is preferably used. An effect obtained by surface-treating the core beads with a lipophilic treatment agent can be evaluated by, for example, confirming the wettability of the resin beads to various types of cosmetic base materials and the water repellency of the resin beads.

Next, a method for producing the above-described resin beads will be described. The method for producing resin beads of the present invention is a method for producing the above-described resin beads and includes a step (suspension preparation step) of mixing an oil phase (first liquid) containing a cellulose ester and an organic solvent that dissolves the cellulose ester with an aqueous phase (second liquid) containing a dispersion stabilizer, thereby preparing a suspension containing oil droplets containing the cellulose ester and the organic solvent.

In the suspension preparation step, the oil phase containing a cellulose ester and an organic solvent that dissolves the cellulose ester is mixed with the aqueous phase containing a dispersion stabilizer. By mixing and, if necessary, stirring the oil phase and the aqueous phase, the suspension in which the oil droplets containing the cellulose ester and the organic solvent are dispersed in water can be obtained. The oil droplets are present in a dispersed state in water, and therefore the organic solvent in the oil droplets transfers gradually into water. Then, the oil droplets contract accompanying the transfer of the organic solvent, so that the cellulose ester dissolved in the organic solvent precipitates gradually. The precipitated cellulose ester grows while retaining smooth surfaces. Finally, the precipitated cellulose ester is fixed, and resin particles which are precursors for substantially solid core beads and resin beads are formed. Whether the contraction of the oil droplets has occurred or not can be decided by analyzing an image observed using an optical microscope, an electron microscope, or the like. When such contraction of the oil droplets occurs, core beads and resin beads which have high sphericity (degree of sphericity), which are substantially solid, which have smooth surfaces, and which have a desired particle size can thereby be obtained.

The cellulose ester is used, as a natural cellulose derivative, for products, such as a cosmetic. As the cellulose ester, at least one selected from a cellulose organic acid ester and a cellulose phosphoric acid ester is preferably used. More specifically, as the cellulose ester, at least one selected from the group consisting of cellulose acetate, cellulose propionate, cellulose acetate propionate, cellulose butyrate, and cellulose acetate butyrate is preferably used.

By hydrolyzing, under an appropriate condition, at least part of ester bonds in the cellulose ester contained in the resin for forming resin particles, core beads and resin beads having a degree of sphericity, a degree of surface smoothness, and a degree of solidity which are suitable for the cosmetic application can be obtained. That is, by appropriately controlling the conditions in hydrolysis, defects which are likely to occur in preparing the core beads containing a resin containing cellulose as a main component are suppressed and resin beads that can suitably be blended in a cosmetic and the like can be produced.

As the cellulose ester, a cellulose ester in which the content of an acyl group, such as an acetyl group, a propionyl group, and a butyroyl group, is 60% by mass or less is preferably used. Among others, cellulose acetate or cellulose acetate propionate in which the content of the acyl group is 60% by mass or less is preferably used. In addition, a cellulose ester such that the viscosity of a 6%-by-mass acetone solution is 200 mPa·s or lower is preferably used. When these cellulose esters are used, a defect and the like are unlikely to occur in the particle size distribution and tactile impression of resultant core beads and resin beads, and resin beads that can suitably be blended in a cosmetic and the like can be obtained more easily.

As the organic solvent (first organic solvent) contained in the oil phase, a known organic solvent which can dissolve the cellulose ester can be used. As the specific examples of the organic solvent, ester-based solvents, such as methyl formate, ethyl formate, methyl acetate, ethyl acetate, and butyl acetate; ketone-based solvents, such as acetone, methyl ethyl ketone, methyl isobutyl ketone, and cyclohexanone; alcohols, such as ethanol and n-butanol; ether-based solvents, such as ethyl cellosolve, butyl cellosolve, and ethylene glycol diethyl ether; glycol ether-based solvents, such as dipropylene glycol monomethyl ether; glycol ester-based solvents, such as propylene glycol monomethyl ether acetate; chlorine-based solvents, such as methylene chloride, chloroform, and tetrachloroethane; nitromethane; propylene carbonate, and the like can be used. These organic solvents can be used singly, or two or more of these organic solvents can be used in combination.

The organic solvent is preferably a ketone-based solvent, an ester-based solvent, an alcohol, a glycol, an ether-based solvent, a halogenated alkyl, or a nitrated alkyl. Among others, the organic solvent is more preferably methyl ethyl ketone, ethyl acetate, butanol, propylene glycol monobutyl ether, propyl acetate, or propylene glycol monomethyl ether acetate.

The organic solvent in the oil droplets contained in the suspension transfers gradually into the aqueous phase. However, when the water-solubility of the organic solvent is too high, the organic solvent is likely to transfer rapidly from the oil droplets into the aqueous phase, and therefore the resin particles which are formed by the contraction of the oil droplets and which are precursors for the core beads may be unlikely to have a perfectly spherical shape, or a smooth surface may be unlikely to be formed. In addition, when the water-solubility of the organic solvent is too high, the aqueous phase is likely to penetrate partially into the oil droplets, so that solid core beads and resin particles may be unlikely to be formed. On the other hand, when the water-solubility of the organic solvent is too low, there is a tendency that the transfer speed of the organic solvent from the oil droplets into the aqueous phase is lowered and a large amount of aqueous phase needs to be used, so that the resin beads may be disadvantageous in terms of production costs. In addition, when the water-solubility of the organic solvent is too low, the organic solvent may be likely to be left in the resin beads. For this reason, the solubility (water-solubility) of the organic solvent to 100 g of water at 25° C. is 0.1 to 50.0 g, preferably 0.5 to 40.0 g, and more preferably 1.0 to 30.0 g.

The liquid amount of the organic solvent contained in the oil phase (first liquid) is preferably 2.0 times or more, more preferably 2.5 to 15.0 times, based on the amount of the cellulose ester on a mass basis. If the liquid amount of the organic solvent in the oil phase is too small, the cellulose ester is likely to precipitate rapidly when the organic solvent in the oil droplets transfers into the aqueous phase. For this reason, core beads and resin beads to be obtained may be unlikely to have a perfectly spherical shape, or a smooth surface may be unlikely to be formed.

The aqueous phase that is used in the suspension preparation step is a liquid (second liquid) in which a dispersion stabilizer is dissolved in water, such as deionized water. As the dispersion stabilizer, water-soluble polymers, such as water-soluble cellulose, polyvinyl alcohol, and sodium polyacrylate; and inorganic salts, such as hydroxyapatite, tribasic calcium phosphate, and calcium carbonate, can be used. These dispersion stabilizers can be used singly, or two or more of these dispersion stabilizers can be used in combination. Among these dispersion stabilizers, a water-soluble polymer, such as water-soluble cellulose, polyvinyl alcohol, or sodium polyacrylate, is preferably used.

To suppress break or coalescence of the oil droplets in the suspension during transportation, it is preferable that the type and concentration of the dispersion stabilizer which is used in the aqueous phase are set appropriately. The content of the dispersion stabilizer in the aqueous phase is preferably 30% by mass or less, more preferably 1 to 20% by mass.

It is preferable that the aqueous phase further contains a second organic solvent. The organic solvent (first organic solvent) in the oil phase may transfer rapidly into the aqueous phase depending on the type. Accordingly, by mixing the aqueous phase containing the second organic solvent with the oil phase, the rapid transfer of the first organic solvent in the oil phase into the aqueous phase can be suppressed, so that core beads and resin beads each having a higher degree of sphericity and having a smoother surface can be produced. As the second organic solvent, any of the above-described organic solvents (first organic solvents) which can be used in the oil phase, including preferred first organic solvents, can be used. Note that the first organic solvent and the second organic solvent may be of the same types or of different types.

In the suspension preparation step, the suspension is prepared by mixing the oil phase and the aqueous phase. To mix the oil phase and the aqueous phase, the oil phase may be added to the aqueous phase under stirring, or the aqueous phase may be added to the oil phase under stirring. The particle sizes of the oil droplets to be formed are preferably adjusted using an emulsification apparatus, such as a disper or a homogenizer, as necessary. The particle sizes of the oil droplets to be formed can easily be adjusted by, for example, changing the number of revolutions of a homogenizer to adjust the shear force. As a result, the particle sizes of the core beads and resin beads to be obtained can appropriately be adjusted in such a way as to fall within a desired range.

The liquid amount of the aqueous phase is preferably set to 3.0 times or less, and more preferably 0.2 to 2.8 times, based on the liquid amount of the oil phase on a mass basis. By setting the liquid amount of the aqueous phase to the above-described range, the rapid transfer of the organic solvent in the oil droplets into the aqueous phase can be suppressed, so that core beads and resin beads each having a higher degree of sphericity and having a smoother surface can be produced.

The method for producing resin beads of the present invention further includes a step (contraction step) of adding water to the suspension, thereby contracting the oil droplets and forming resin particles. By adding water to the suspension, the oil droplets in the suspension can be contracted more quickly and the resin particles which are precursors for the core beads and the resin beads can be formed. The liquid amount of water to be added to the suspension is preferably 0.5 times or more, more preferably 1 to 100 times, based on the liquid amount of the suspension on a mass basis.

In the contraction step, water is preferably added to the suspension over a time of about 10 minutes or longer. By adding water over a time of 10 minutes or longer, the rapid transfer of the organic solvent in the oil droplets into the aqueous phase can be suppressed, so that resin particles, core beads, and resin beads each having a higher degree of sphericity and having a smoother surface can be produced. Specifically, water is preferably added to the suspension over 30 minutes or longer, water is more preferably added over 45 minutes or longer, and water is particularly preferably added over 60 to 300 minutes.

The method for producing resin beads of the present invention further includes a step (hydrolysis step) of treating the resin particles formed in the above-described contraction step under an acidic condition, or an alkaline condition of a pH of 13 or lower, thereby hydrolyzing at least part of ester bonds in the cellulose ester. Thereby, core beads being precursors for resin beads which are formed with a resin containing cellulose as a main component, which have a desired degree of sphericity, degree of surface smoothness, and degree of solidity, and which exhibit favorable biodegradability can be obtained.

In the case where the resin particles are treated under an alkaline condition, pH is 13 or lower, preferably 8 to 13. When pH is higher than 13, cellulose produced by the hydrolysis of the ester bonds is likely to aggregate, so that core beads and resin beads having desired properties cannot be obtained. In addition, in the case where the resin particles are treated under an acidic condition, pH is preferably 1.5 to 6, more preferably 1.8 to 5.5.

The temperature during the hydrolysis is preferably set to 100° C. or lower. That is, at least part of the ester bonds in the cellulose ester is preferably hydrolyzed by treating the resin particles under a temperature condition of 100° C. or lower, more preferably under a temperature condition of 0 to 90° C., and particularly preferably at 10 to 80° C. The degree (degree of progress) of the hydrolysis of the ester bonds can be monitored by infrared spectroscopy (IR) whenever necessary. Neutralization may be performed by adding an acid or an alkali after checking the degree (degree of progress) of the hydrolysis.

After the hydrolysis, unnecessary components are removed by, for example, subjecting the produced core beads to filtration and washing. Subsequently, washing is repeated multiple times as necessary, and then drying and a disintegration treatment are performed, and thereby core beads which are precursors for the resin beads can be obtained.

The method for producing resin beads of the present invention includes a step (surface treatment step) of surface-treating, with a surface treatment agent, the core beads obtained in the above-described hydrolysis step. In this surface treatment step, 100 parts by mass of the core beads are preferably surface-treated with 0.1 to 30 parts by mass, more preferably 0.5 to 20 parts by mass, and particularly preferably 1 to 10 parts by mass, of a surface treatment agent. By setting the amount of the surface treatment agent based on the amount of the core beads, which are objects to be treated, to the above-described range, resin beads having more excellent tactile impression, such as spreadability on the skin, moist feeling, and softness, which are required in resin beads to be blended in a cosmetic and the like, and having higher stability can be provided.

The surface treatment agent is preferably a plate-shaped substance. The "plate-shaped substance" herein refers to a substance having a ratio of the major axis to the minor axis (major axis/minor axis) of more than 1 and a ratio of the major axis to the thickness (major axis/thickness' of 2 or more. The plate-shaped substance elaborately exhibits its chemical characteristics owing to the surfaces, and, because of having a given thickness, can surface-treat an object to be treated in a physically and chemically stable manner. For this reason, by using a plate-shaped substance as the surface treatment agent, novel properties can be imparted to the core beads more stably. Note that the aspect ratio (major axis/minor axis) of the plate-shaped substance is preferably 2 or more and 10 or less, more preferably 8 or less, and particularly preferably 5 or less.

When the core beads having a high degree of sphericity and a high degree of surface smoothness are surface-treated, the surfaces of the core beads can be coated in an extremely dense manner, and therefore the physical stability and chemical effects of the resultant resin beads can be enhanced more. Further, by surface-treating the core beads with a plate-shaped substance, the above-described effects in particular can be enhanced. In contrast, beads obtained by directly adjusting the shape of cellulose into a spherical shape or beads reproduced by a viscose process have a low degree of sphericity and a low degree of surface smoothness, and therefore when such beads are surface-treated by, for example, a dry process, the recessed parts on the surfaces of the beads may be left untreated or the sticking properties may be lowered. Further, with regard to the beads obtained by directly adjusting the shape of cellulose into a spherical shape or the beads reproduced by a viscose process, intramolecular hydrogen bond is strong. For this reason, it is considered that the chemical adsorption stability of a surface treatment agent to these beads is likely to be lowered and the effects of the surface treatment are likely to be lowered.

In the method for producing resin beads of the present invention, resin particles in which a cellulose ester, which is used as a raw material, is fixed, with the hydrogen bond being weak, into a perfectly spherical shape are formed, and then the ester sites of the resin particles are hydrolyzed relatively slowly to obtain the core beads formed with a resin containing a cellulose as a main component, and the core beads are then surface-treated. For this reason, it is considered that hydrogen bond between cellulose molecules is suppressed, and therefore it is considered that hydrogen bonding force between the cellulose molecules and the surface treatment agent can be enhanced and the effects of the surface treatment can be improved more.

The average grain size of the plate-shaped substance which is used as the surface treatment agent is preferably 5.0 μm or smaller, more preferably 1.0 μm or smaller. In addition, the average thickness of the plate-shaped substance is preferably 1.0 μm or less, more preferably 0.5 μm or less. As the thickness of the plate-shaped substance is thinner or as the grain size of the plate-shaped substance is smaller, the surfaces of the core beads can be coated more densely, and therefore the physical stability and chemical effects can be enhanced more. The average grain size of the plate-shaped substance is an arithmetic average value of the values obtained through measurement with a particle size distribution analyzer. The aspect ratio (major axis/minor axis) of the plate-shaped substance is calculated using arithmetic average values of the major axes and the minor axes of 10 or more plate-shaped substances arbitrarily selected in a SEM image (×5,000) of the plate-shaped substances, taken with a scanning electron micrograph (SEM). The thickness of the plate-like substance is calculated as the arithmetic average value of the thicknesses of 10 or more plate-shaped substances arbitrarily selected in a SEM image (×5,000) of the plate-shaped substances, taken with a scanning electron micrograph (SEM).

The resin beads can be obtained by surface-treating the core beads making use of adhesion, ionic bond, covalent bond, or the like of the surface treatment agent. Specific examples of the surface treatment include dry blending (dry process), a wet process, a gas-phase treatment, a spray-drying treatment, and a mechanochemical treatment. The mechanochemical treatment is one of the methods for treating a solid with a solid and is a treatment making use of the surface activity or surface charge of the particles by means of pulverization, grinding, friction, or the like that causes the structure and bonding state of a substance to change. Among the above-described surface treatments, the dry blending treatment and the mechanochemical treatment are preferable.

The above-described resin beads are resin particles which have high sphericity (degree of sphericity), which are solid, which have a smooth surface and exhibit excellent biodegradability, and which are obtained using a natural material as a constituent material. For this reason, various types of products, such as a cosmetic, a dermatological preparation, a paint, a shaped article, a film, a coating agent, and a resin composition, which have excellent tactile impression, such as spreadability on the skin, moist feeling, and softness, and which have high stability such that such tactile impression is kept over a long period of time, can be provided without using resin particles composed of a synthetic material derived from petroleum by allowing the above-described resin beads to be contained in the products.

EXAMPLES

Hereinafter, the present invention will specifically be described based on Examples, but the present invention is not limited to these Examples. Note that "parts" and "%" in Examples and Comparative Examples are on a mass basis unless otherwise noted.

<Production of Resin Beads>

Example 1

An oil phase was prepared by dissolving 150 parts of cellulose acetate (trade name "CA-398-6," manufactured by Eastman Chemical Company, content ratio of acetyl group: 39.8%) in 1,350 parts of ethyl acetate (water-solubility: 8 g/100 g). In addition, an aqueous phase was prepared by dissolving 100 parts of polyvinyl alcohol in 1,250 parts of ion-exchanged water. The oil phase was added to and mixed with the prepared aqueous phase, and the resultant mixture was stirred using a dissolver at 1,000 rpm for 3 minutes. The mixture was further stirred using the dissolver at 2,000 rpm for 10 minutes to obtain a suspension in which oil droplets were dispersed uniformly. The volume average particle size of the oil droplets, as measured through observation with an optical microscope and image analysis, was 18 μm.

A resin particle dispersion was obtained by pouring 42,000 parts of ion-exchanged water into the obtained suspension over 90 minutes while the suspension was being stirred using the dissolver at 500 rpm. The resin particles were subjected to filtration and washing, and then deflocculated in ion-exchanged water and stirred. Resin particles obtained through filtration and washing were dispersed in 2,500 parts of ion-exchanged water. Sodium hydroxide was added to adjust pH of the dispersion to 13.0 or lower and the dispersion was heated to 50° C. to perform hydrolysis reaction. After the hydrolysis reaction was completed, the reaction solution was neutralized with hydrochloric acid. The product was subjected to filtration and washing, and then deflocculated in ion-exchanged water. Further, the product was subjected to filtration and washing, and then subjected to drying and a disintegration treatment to obtain core beads having a median size ($D_{50}$) of 9 μm.

In a small-sized mixer, 50 g of the obtained core beads and 1.5 g of zinc stearate (trade name "SPZ-100F," manufactured by SAKAI CHEMICAL INDUSTRY CO., LTD., plate-shaped powder, average grain size 0.4 μm, thickness 0.1 µm, aspect ratio 3) were placed and dry-mixed for 3 minutes to surface-treat the core beads with zinc stearate, and thus resin beads were obtained. The FIGURE shows an electron micrograph that shows a state of the surfaces of the obtained resin beads.

Example 2

Resin beads were obtained in the same manner as in Example 1 described above, except that 2.5 g of magnesium stearate (trade name "SPX-100F," manufactured by SAKAI CHEMICAL INDUSTRY CO., LTD., plate-shaped powder, average grain size 0.7 µm, thickness 0.1 µm, aspect ratio 4) was used in place of zinc stearate.

Example 3

Resin beads were obtained in the same manner as in Example 1 described above, except that 1.5 g of zinc myristate (plate-shaped powder, average grain size 0.6 µm, thickness 0.1 µm, aspect ratio 3) synthesized by an ordinary method was used in place of zinc stearate.

Reference Example 4

To 1,000 g of ion-exchanged water, 50 g of the core beads prepared in Example 1 were added, and then the resultant mixture was subjected to a dispersion treatment with a homogenizer for 10 minutes to obtain a dispersion. To the obtained dispersion, 50 g of a 5% aqueous sodium laurate solution was added, and the resultant mixture was sufficiently stirred, and then an excess amount of magnesium chloride was added to surface-treat the core beads with magnesium laurate. After neutralization was performed, the product was subjected to filtration and washing. Further, the product was subjected to drying and a disintegration treatment to obtain resin beads.

Example 5

An oil phase was prepared by dissolving 200 parts of cellulose acetate propionate (trade name "CAP-482-0.5," manufactured by Eastman Chemical Company, total content ratio of acetyl group and propionyl group: 46.5%) in 1,000 parts of ethyl acetate (water-solubility: 8 g/100 g). In addition, an aqueous phase was prepared by dissolving 100 parts of polyvinyl alcohol in 1,150 parts of ion-exchanged water. The oil phase was added to and mixed with the prepared aqueous phase, and the resultant mixture was stirred using a dissolver at 1,000 rpm for 3 minutes. The mixture was further stirred using the dissolver at 1,800 rpm for 5 minutes to obtain a suspension in which oil droplets were dispersed uniformly. The volume average particle size of the oil droplets, as measured through observation with an optical microscope and image analysis, was 17 µm.

A resin particle dispersion was obtained by pouring 22,550 parts of ion-exchanged water into the obtained suspension over 90 minutes while the suspension was being stirred using the dissolver at 500 rpm. The resin particles were subjected to filtration and washing, and then deflocculated in ion-exchanged water and stirred. The resin particles were subjected to filtration and washing, and then subjected to drying and a disintegration treatment to obtain resin particles. The obtained resin particles were dispersed in 5,000 parts of ion-exchanged water. Sodium hydroxide was added to adjust pH of the dispersion to 13.0 or lower and the dispersion was heated to 45° C. to perform hydrolysis reaction. After the hydrolysis reaction was completed, the reaction solution was neutralized with acetic acid. The product was subjected to filtration and washing, and then deflocculated in ion-exchanged water. Further, the product was subjected to filtration and washing, and then subjected to drying and a disintegration treatment to obtain core beads having a median size ($D_{50}$) of 8 µm.

In a small-sized mixer, 100 g of the obtained core beads and 7.0 g of calcium stearate (trade name "NISSAN ELECTOL MC-2," manufactured by NOF CORPORATION, plate-shaped powder, average grain size 2.0 µm, thickness 0.1 µm, aspect ratio 2) were placed and dry-mixed for 3 minutes to surface-treat the core beads with calcium stearate, and thus resin beads were obtained.

Example 6

An oil phase was prepared by dissolving 89 parts of cellulose acetate propionate (trade name "CAP-504-0.2," manufactured by Eastman Chemical Company, total content ratio of acetyl group and propionyl group: 43.0%) in 1,000 parts of 1-butanol (water-solubility: 8 g/100 g). To the prepared oil phase, 10 parts of fine particle titanium oxide (trade name "MT-100TV," manufactured by TAYCA CORPORATION), treated with a fatty acid, and 1 part of an acrylic silicone dispersant (trade name "KP-578," manufactured by Shin-Etsu Chemical Co., Ltd.) were added, and the resultant mixture was mixed to disperse the fine particle titanium oxide in the oil phase. In addition, an aqueous phase was prepared by dissolving 60 parts of polyacrylic acid in 940 parts of ion-exchanged water. The oil phase was added to and mixed with the prepared aqueous phase, and the resultant mixture was stirred using a dissolver at 1,000 rpm for 3 minutes. The mixture was further stirred using the dissolver at 2,800 rpm for 20 minutes to obtain a suspension in which oil droplets were dispersed uniformly. The volume average particle size of the oil droplets, as measured through observation with an optical microscope and image analysis, was 8 µm.

A resin particle dispersion was obtained by pouring 68,000 parts of ion-exchanged water into the obtained suspension over 240 minutes while the suspension was being stirred using the dissolver at 500 rpm. The resin particles were subjected to filtration and washing, and then deflocculated in ion-exchanged water and stirred. The resin particles were subjected to filtration and washing, and then subjected to drying and a disintegration treatment to obtain resin particles. The obtained resin particles were dispersed in 5,000 parts of ion-exchanged water. Sodium hydroxide was added to adjust pH of the dispersion to 13.0 or lower and the dispersion was heated to 55° C. to perform hydrolysis reaction. After the hydrolysis reaction was completed, the reaction solution was neutralized with acetic acid. The product was subjected to filtration and washing, and then deflocculated in ion-exchanged water. Further, the product was subjected to filtration and washing, and then subjected to drying and a disintegration treatment to obtain core beads having a median size ($D_{50}$) of 4 µm.

In a small-sized mixer, 50 g of the obtained core beads and 5.5 g of zinc stearate (trade name "SPZ-100F," manufactured by SAKAI CHEMICAL INDUSTRY CO., LTD., plate-shaped powder, average grain size 0.4 µm, thickness 0.1 µm, aspect ratio 3) were placed and dry-mixed for 3 minutes to surface-treat the core beads with zinc stearate, and thus resin beads were obtained.

Comparative Example 1

Cellulose fine particles (trade name "CELLULOBEADS D-5," manufactured by DAITO KASEI KOGYO CO., LTD.) were used as resin beads of Comparative Example 1.

Comparative Example 2

The core beads (not surface-treated) prepared in Example 1 were used as resin beads of Comparative Example 2.

Comparative Example 3

The core beads (not surface-treated) prepared in Example 5 were used as resin beads of Comparative Example 3.

Comparative Example 4

An oil phase was prepared by dissolving 100 parts of cellulose acetate propionate (trade name "CAP-482-0.5," manufactured by Eastman Chemical Company, total content ratio of acetyl group and propionyl group: 46.5%) in 700 parts of ethyl acetate (water-solubility: 8 g/100 g). In addition, an aqueous phase was prepared by dissolving 40 parts of polyvinyl alcohol in 760 parts of ion-exchanged water. The oil phase was added to and mixed with the prepared aqueous phase, and the resultant mixture was stirred using a dissolver at 1,000 rpm for 3 minutes. The mixture was further stirred using the dissolver at 1,950 rpm for 8 minutes to obtain a suspension in which oil droplets were dispersed uniformly. The volume average particle size of the oil droplets, as measured through observation with an optical microscope and image analysis, was 20 μm.

A resin particle suspension was obtained by pouring 16,000 parts of ion-exchanged water into the obtained suspension over 100 minutes while the suspension was being stirred using the dissolver at 500 rpm. The resin particles were subjected to filtration and washing, and then deflocculated in ion-exchanged water and stirred. Resin particles obtained through filtration and washing were dispersed in 3,000 parts of ion-exchanged water. Sodium hydroxide was added to adjust pH of the dispersion to 13.5 and the dispersion was heated to 65° C. to perform hydrolysis reaction. After the hydrolysis reaction was completed, the reaction solution was neutralized with acetic acid. The product was subjected to filtration and washing, and then deflocculated in ion-exchanged water. Further, the product was subjected to filtration and washing, and then subjected to drying and a disintegration treatment to obtain core beads having a median size ($D_{50}$) of 17.5 μm.

In a small-sized mixer, 50 g of the obtained core beads and 2.5 g of magnesium stearate (trade name "SPX-100F," manufactured by SAKAI CHEMICAL INDUSTRY CO., LTD., plate-shaped powder, average grain size 0.7 μm, thickness 0.1 μm, aspect ratio 4) were placed and dry-mixed for 3 minutes to surface-treat the core beads with magnesium stearate, and thus resin beads were obtained.

<Evaluation of Resin Beads>

(Particle Size and Coefficient of Variation (CV Value))

The cumulative 50% particle size ($D_{50}$) on a volume basis, cumulative 10% particle size ($D_{10}$) on a volume basis, and cumulative 90% particle size ($D_{90}$) on a volume basis of the resin beads were measured using Coulter Counter (manufactured by Beckman Coulter, Inc.), and the coefficient of variation (CV value) of the particle size was calculated. Results are shown in Table 1.

(Degree of Sphericity)

A SEM image of the resin beads, taken with a scanning electron microscope (SEM), was subjected to image analysis to calculate the degree of circularity C for each resin bead from the following formula (1). Then, the arithmetic average value of the degrees of circularity C for 10 or more resin beads arbitrarily selected was defined as the degree of sphericity. Results are shown in Table 1.

$$C=(4\pi S_1)/(L^2) \qquad (1)$$

In the formula (1), $S_1$ represents the area (projected area) of each resin bead in the image, and L represents the length of the outer peripheral part of the resin bead in the image. As the value of the degree of circularity C is closer to 1, the shape of a particle is closer to a perfect sphere.

(Degree of Surface Smoothness)

A SEM image (×5,000) of the resin beads, taken with a scanning electron microscope (SEM), was observed to calculate the degree of smoothness M for each resin bead from the following formula (2). Then, the arithmetic average value of the degrees of smoothness M for 10 or more resin beads arbitrarily selected was defined as the degree of surface smoothness. Results are shown in Table 1. As the value of the degree of smoothness M is closer to 100, the surface of a particle is closer to be smooth.

$$M=(1-(S_3)/(S_2))\times 100 \qquad (2)$$

In the formula (2), $S_2$ represents the area (projected area) of each resin bead in the image, and in the case where a resin bead and a circle that approximates the resin bead are overlapped, $S_3$ represents, in the regions formed by the contour of the resin bead and the contour of the circle, the sum total of the areas of regions that exist inside the contour of the overlapped circle and the areas of regions that exist outside the contour of the overlapped circle.

(Degree of Crystallinity)

Peak intensity (P) at around 2θ=12° and peak intensity (PB) of the base line there were determined among the cellulose type II diffraction peaks of the resin beads, measured with an X-ray diffractometer. Then, the degree of crystallinity C of the resin beads was calculated from the following formula (3). Results are shown in Table 1. As the value of the degree of crystallinity C is closer to 100, the degree of crystallinity of the resin beads is higher.

$$C=\{(P-PB)/PB\}\times 100 \qquad (3)$$

(Degree of Solidity)

A SEM image of sections of the resin beads, taken with a scanning electron microscope (SEM), was subjected to image analysis to calculate the volume of the part filled with the resin for each resin bead. Then, the average value of the volumes of the parts filled with the resin for 10 or more resin beads arbitrarily selected was defined as the degree of solidity (% by volume). Results are shown in Table 1.

(Content of Cellulose)

The content of the cellulose in the resin forming the resin beads was measured by infrared absorption spectroscopy. Specifically, some mixtures each containing the cellulose and the cellulose ester at an arbitrary ratio were prepared to make a calibration curve based on the peak intensity of a carboxylic acid at around 1750 $cm^{-1}$. Then, the content of the cellulose in the resin forming the resin beads (core beads) was calculated using this calibration curve. Calculated contents of the cellulose are shown in Table 1. Note that when the absorption peaks of the surface treatment agent and those of the mixtures were overlapped, measurement was performed after the surface treatment agent was removed.

TABLE 1

(Tactile Impression)

| | $D_{50}$ (μm) | Degree of sphericity | Degree of crystallinity (%) | $D_{90}$ (μm) | $D_{10}$ (μm) | CV value (%) | Degree of surface smoothness (%) | Degree of solidity (%) | Content (%) of cellulose |
|---|---|---|---|---|---|---|---|---|---|
| Example 1 | 9.0 | 0.96 | 21.4 | 18.0 | 5.0 | 51 | 92 | 94 | 100 |
| Example 2 | 9.0 | 0.96 | 21.4 | 18.0 | 5.0 | 51 | 92 | 94 | 100 |
| Example 3 | 9.0 | 0.96 | 21.4 | 18.0 | 5.0 | 51 | 92 | 94 | 100 |
| Reference Example 4 | 9.0 | 0.96 | 21.4 | 18.0 | 5.0 | 51 | 92 | 94 | 100 |
| Example 5 | 8.0 | 0.95 | 32.7 | 14.1 | 4.1 | 51 | 96 | 85 | 100 |
| Example 6 | 4.0 | 0.98 | 32.1 | 7.2 | 2.2 | 48 | 97 | 97 | 89 |
| Comparative Example 1 | 13.0 | 0.67 | 68.0 | 27.0 | 9.1 | 50 | 62 | 66 | 100 |
| Comparative Example 2 | 9.0 | 0.96 | 21.4 | 18.0 | 5.0 | 51 | 92 | 94 | 100 |
| Comparative Example 3 | 8.0 | 0.95 | 32.7 | 14.1 | 4.1 | 51 | 96 | 85 | 100 |
| Comparative Example 4 | 17.5 | 0.50 | 64.1 | 46.4 | 8.4 | 70 | 51 | 88 | 100 |

Sensory evaluation on the tactile impression for the resin beads by a panel test of ten people was performed. Each of "spreadability on the skin," "moist feeling," and "softness" was totally decided when the resin beads were touched, and was graded on a scale of 1 to 5 according to the evaluation criteria shown below to calculate the average mark in ten people. Results are shown in Table 2.
- 5: Excellent
- 4: Above average
- 3: Average
- 2: Below average
- 1: Poor (Water Repellency)

The lipophilicity of the resin beads was evaluated by the water repellency of the resin beads. Specifically, 20 mL of ion-exchanged water was put into a 50 mL test tube, and further, 0.5 g of the resin beads were put therein, and then the resultant mixture was lightly stirred with a spatula. After one day, the contents in the test tube were observed and the water repellency of the resin beads was evaluated according to the evaluation criteria shown below. Results are shown in Table 2.
- 5: Beads are completely floating.
- 4: A slight number of beads are settled.
- 3: There are settled beads.
- 2: Most of the beads are settled
- 1: All the beads are settled.

(Biodegradation Rate)

The biodegradation rate (after 5 days) of the resin beads was measured and calculated in accordance with JIS K6950: 2000 (ISO 14851:1999). Results are shown in Table 2.

<Production of Cosmetic>

TABLE 2

| | Spreadability on skin | Moist feeling | Softness | Water repellency | Biodegradation rate (%) |
|---|---|---|---|---|---|
| Example 1 | 4.5 | 4.5 | 4.5 | 5 | 49 |
| Example 2 | 4.4 | 4.4 | 4.4 | 5 | 48 |
| Example 3 | 4.3 | 4.3 | 4.3 | 5 | 49 |
| Reference Example 4 | 4.0 | 4.1 | 3.9 | 4 | 49 |
| Example 5 | 4.7 | 4.7 | 4.7 | 5 | 49 |
| Example 6 | 4.5 | 4.5 | 4.5 | 5 | 49 |
| Comparative Example 1 | 2.1 | 1.2 | 1.2 | 1 | 31 |
| Comparative Example 2 | 2.5 | 1.2 | 1.2 | 1 | 48 |
| Comparative Example 3 | 2.4 | 1.2 | 1.2 | 1 | 49 |
| Comparative Example 4 | 2.3 | 2.4 | 2.3 | 2 | 45 |

(Cosmetic-1)

Cosmetic-1, which is liquid foundation, was produced according to a known method by blending components which had conventionally been used as raw materials for cosmetics according to blending amounts shown in Table 3.

TABLE 3

| Component name | Blending amount (parts) |
|---|---|
| Resin beads | 10.0 |
| Propylene glycol | 5.0 |
| Bentonite | 1.0 |
| Triethanolamine | 1.0 |
| Stearic acid | 3.0 |
| Stearyl alcohol | 1.0 |
| Liquid paraffin | 8.0 |
| Isopropyl myristate | 5.0 |
| Vaseline | 2.0 |
| Stearic acid monoglyceride | 2.0 |
| POE (20) stearyl ether | 1.0 |
| Titanium oxide | 8.0 |
| Kaolin | 5.0 |
| Iron oxide | 0.5 |
| Antiseptic | 0.5 |
| Perfume | 0.3 |
| Purified water | Balance |
| Total | 100.0 |

(Cosmetic-2)

Cosmetic-2, which is a milky lotion, was produced according to a known method by blending components which had conventionally been used as raw materials for cosmetics according to blending amounts shown in Table 4.

TABLE 4

| Component name | Blending amount (parts) |
| --- | --- |
| Resin beads | 2.0 |
| Propylene glycol | 5.0 |
| Polyethylene glycol 1500 | 3.0 |
| Carboxyvinyl polymer | 0.1 |
| Triethanolamine | 1.0 |

TABLE 4-continued

| Component name | Blending amount (parts) |
| --- | --- |
| Stearic acid | 2.0 |
| Cetyl alcohol | 1.5 |
| Liquid paraffin | 10.0 |
| Vaseline | 3.0 |
| Oleic acid monoglyceride | 1.0 |
| POE (20) sorbitan monoglyceride | 1.0 |
| Antiseptic | 0.2 |
| Perfume | 0.1 |
| Purified water | Balance |
| Total | 100.0 |

<Evaluation of Cosmetic-1>
(Tactile Impression and Spreadability on Skin)

Sensory evaluation on the tactile impression and the spreadability on the skin for cosmetic-1 by a panel test of ten people was performed. The "tactile impression" and the "spreadability on the skin" were decided and graded on a scale of 1 to 5 according to the evaluation criteria shown below to calculate the average mark in ten people. Results are shown in Table 5.

5: Excellent
4: Above average
3: Average
2: Below average
1: Poor (Stability)

In a 30 mL sealable glass bottle, 4.0 g of cosmetic-1 was placed, and an accelerated test was performed in such a way that the glass bottle was sealed and stored in a thermostatic chamber set at 50° C. for 7 days, and then the temperature was returned to room temperature. Sensory evaluation on the "tactile impression" for cosmetic-1 before and after the accelerated test by a panel test of ten people was performed. The "tactile impression" was graded based on the "tactile impression" before the accelerated test as the standard on a scale of 1 to 5 according to the evaluation criteria shown below to calculate the average mark in ten people. Results are shown in Table 5.

5: Change is not felt.
4: Change is somewhat felt.
3: Change is felt.
2: Somewhat strong change is felt.
1: Strong change is felt.

TABLE 5

| Cosmetic-1 | Resin beads | Tactile impression | Spreadability on skin | Stability |
| --- | --- | --- | --- | --- |
| Example A1 | Example 1 | 4.7 | 4.7 | 4.8 |
| Example A2 | Example 2 | 4.8 | 4.8 | 4.8 |
| Example A3 | Example 3 | 4.6 | 4.7 | 4.8 |
| Reference Example A4 | Reference Example 4 | 4.1 | 4.0 | 4.1 |
| Example A5 | Example 5 | 4.6 | 4.6 | 4.6 |
| Example A6 | Example 6 | 4.4 | 4.5 | 4.6 |
| Comparative Example A1 | Comparative Example 1 | 1.7 | 1.7 | 1.5 |
| Comparative Example A2 | Comparative Example 2 | 2.1 | 1.9 | 1.6 |
| Comparative Example A3 | Comparative Example 3 | 2.0 | 1.8 | 1.6 |
| Comparative Example A4 | Comparative Example 4 | 2.3 | 2.2 | 2.4 |

<Evaluation of Cosmetic-2>
(Tactile Impression and Spreadability on Skin)

Sensory evaluation on the tactile impression and the spreadability on the skin for cosmetic-2 by a panel test of ten people was performed. The "tactile impression" and the "spreadability on the skin" were decided and graded on a scale of 1 to 5 according to the evaluation criteria shown below to calculate the average mark in ten people. Results are shown in Table 6.

5: Excellent
4: Above average
3: Average
2: Below average
1: Poor (Stability)

In a 30 mL sealable glass bottle, 4.0 g of cosmetic-2 was placed, and an accelerated test was performed in such a way that the glass bottle was sealed and stored in a thermostatic chamber set at 50° C. for 7 days, and then the temperature was returned to room temperature. Sensory evaluation on the "tactile impression" for cosmetic-2 before and after the accelerated test by a panel test of ten people was performed. The "tactile impression" was graded based on the "tactile impression" before the accelerated test as the standard on a scale of 1 to 5 according to the evaluation criteria shown below to calculate the average mark in ten people. Results are shown in Table 6.

5: Change is not felt.
4: Change is somewhat felt.
3: Change is felt.
2: Somewhat strong change is felt.
1: Strong change is felt.

TABLE 6

| Cosmetic-2 | Resin beads | Tactile impression | Spreadability on skin | Stability |
|---|---|---|---|---|
| Example B1 | Example 1 | 4.6 | 4.8 | 4.8 |
| Example B2 | Example 2 | 4.7 | 4.8 | 4.8 |
| Example B3 | Example 3 | 4.6 | 4.8 | 4.8 |
| Reference Example B4 | Reference Example 4 | 4.0 | 4.1 | 4.0 |
| Example B5 | Example 5 | 4.8 | 4.8 | 4.6 |
| Example B6 | Example 6 | 4.6 | 4.5 | 4.6 |
| Comparative Example B1 | Comparative Example 1 | 1.7 | 1.6 | 1.5 |
| Comparative Example B2 | Comparative Example 2 | 2.1 | 2.4 | 2.1 |
| Comparative Example B3 | Comparative Example 3 | 2.0 | 2.3 | 2.2 |
| Comparative Example B4 | Comparative Example 4 | 2.0 | 2.6 | 2.4 |

As shown in Tables 5 and 6, it is understood that cosmetics having excellent spreadability on the skin and moist feeling and having softness and high stability, were able to be produced by using the resin beads of Examples. Further, it was ascertained that properties, such as excellent tactile impression and spreadability, were also able to be imparted not only to a cosmetic but also to various types of products, such as a dermatological preparation, a paint, a shaped article, a film, a coating agent, and a resin composition, by using the resin beads of Examples.

INDUSTRIAL APPLICABILITY

The resin beads of the present invention have properties equal to or superior to those of the resin beads formed with a synthetic material derived from petroleum. For this reason, by using the resin beads of the present invention, products, such as a cosmetic having excellent spreadability on the skin and moist feeling, having softness and high stability, and having favorable biodegradability, can be provided without using the resin beads formed with a synthetic material derived from petroleum. Accordingly, the resin beads of the present invention are useful as a constituent material for various types of products, such as, for example, a cosmetic, a dermatological preparation, a paint, a shaped article, a film, a coating agent, and a resin composition.

The invention claimed is:

1. Resin beads obtained by surface-treating, with a surface treatment agent in solid form, core beads formed with a resin comprising cellulose as a main component, wherein
   an amount of the cellulose in the resin forming the core beads is in a range from 89 to 100 mass % relative to the resin,
   the resin beads have a cumulative 50% particle size on a volume basis in a range of 50 μm or smaller,
   a degree of sphericity in a range from 0.7 to 1.0,
   a degree of surface smoothness in a range from 70 to 100%, and
   a degree of crystallinity in a range of 60% or less.

2. The resin beads according to claim 1, wherein the surface treatment agent is a plate-shaped substance.

3. The resin beads according to claim 2, wherein the plate-shaped substance has an aspect ratio (major diameter/minor diameter) in a range from 2 to 10.

4. The resin beads according to claim 1, wherein the surface treatment agent is at least one lipophilic treatment agent selected from the group consisting of metallic soap-based treatment agents, amino acid-based treatment agents, phospholipid-based treatment agents, glycolipid-based treatment agents, complex lipid-based treatment agents, and ceramide-based treatment agents.

5. The resin beads according to claim 4, wherein the metallic soap-based treatment agents are metal salts of stearic acid.

6. The resin beads according to claim 1, having a biodegradation rate for 5 days, as measured in accordance with JIS K6950:2000 (ISO 14851:1999), in a range of 10% or more.

7. The resin beads according to claim 1, having a cumulative 90% particle size on a volume basis in a range of 40 82 m or smaller.

8. The resin beads according to claim 1, having a cumulative 10% particle size on a volume basis in a range of 0.1 μm or larger.

9. The resin beads according to claim 1, wherein a coefficient of variation (CV) value of the particle size is in a range from 10 to 90%.

10. A product of any one of a cosmetic, a dermatological preparation, a paint, a shaped article, a film, a coating agent, and a resin composition each comprising resin beads, wherein
    the resin beads are the resin beads according to claim 1.

11. d) A method for producing resin beads according to claim 1, having a cumulative 50% particle size on a volume basis in a range of 50 μm or smaller, a degree of sphericity in a range from 0.7 to 1.0, a degree of surface smoothness in a range from 70 to 100%, and a degree of crystallinity in a range of 60% or less, the method comprising:
    mixing an oil phase comprising a cellulose ester and an organic solvent that dissolves the cellulose ester and has a solubility to 100 g of water at 25° C. in a range from 0.1 to 50.0 g, with an aqueous phase comprising a dispersion stabilizer, thereby preparing a suspension comprising oil droplets that comprised the cellulose ester and the organic solvent;
    adding water to the suspension, thereby contracting the oil droplets and forming resin particles;
    treating the resin particles under an acidic condition, or an alkaline condition of a pH of 13 or lower, thereby hydrolyzing at least part of ester bonds in the cellulose ester to obtain core beads formed with a resin comprising cellulose as a main component; and
    surface-treating the core beads with a surface treatment agent in solid form,
    wherein an amount of the cellulose in the resin forming the core beads is in a range from 89 to 100 mass % relative to the resin.

12. The method for producing resin beads according to claim 11, wherein the cellulose ester is at least one material selected from the group consisting of cellulose acetate, cellulose propionate, cellulose acetate propionate, cellulose butyrate, and cellulose acetate butyrate.

13. The method for producing resin beads according to claim 11, wherein the dispersion stabilizer is a water-soluble polymer.

14. The method for producing resin beads according to claim 11, wherein 100 parts by mass of the core beads are surface-treated with 0.1 to 30 parts by mass of the surface treatment agent.

15. The method for producing resin beads according to claim 11, wherein the surface treatment agent is a plate-shaped substance.

16. The method for producing the resin beads according to claim 15, wherein the plate-shaped substance has an aspect ratio (major axis/minor axis) in a range of 10 or less.

17. The method for producing resin beads according to claim 11, wherein the core beads are surface-treated with the surface treatment agent by a dry blending method or a mechanochemical method.

* * * * *